United States Patent [19]

Ponto

[11] Patent Number: Plant 5,862

[45] Date of Patent: Jan. 20, 1987

[54] *RAPHIOLEPIS INDICA* CV. MONTO

[75] Inventor: Bill Ponto, Vista, Calif.

[73] Assignee: Monrovia Nursery Company, Azusa, Calif.

[21] Appl. No.: 733,891

[22] Filed: May 14, 1985

[51] Int. Cl.[4] ..... A01H 5/00

[52] U.S. Cl. ..... Plt./54

[58] Field of Search ..... Plt./54

*Primary Examiner*—Robert E. Bagwill

[57] ABSTRACT

A new and distinct selection of *Raphiolepis indica* (L.) Lindl. shrub (known popularly as Indian Hawthorn) which shall be referred to hereinafter as *Raphiolepis indica* cultivar Monto. *Raphiolepis indica* cultivar Monto is distinct with its combination of large glossy bright green leaves; tomentum covering the new foliage and large single pink flowers fading to a pure white with red filaments.

2 Drawing Figures

DISCOVERY

This invention relates to a new and distinct selection of *Raphiolepis indica,* a member of the rose family, Rosacease. *Raphiolepis indica* cv. Monto was discovered as a chance sport growing among other *Raphiolepis indica* 'Enchantress' at Ponto Nursery, 2545 Ramona Drive, Vista, Calif. in the Spring of 1981.

The plant to date is known to exist only within the boundaries of Monrovia Nursery and Ponto Nursery and has not been offered for sale or described in any publication.

REPRODUCTION

My new selection has been strictly asexually reproduced by cuttings and grafting at Ponto Nursery and Monrovia Nursery Company. Sexual reproduction, such as seed propagation could result in a potential loss of the selected attributes. Therefore, sexual reproduction is prohibited and propagation is restricted to asexual reproduction by vegetative cuttings or grafts. Seed progeny from this new selection has not been observed, though it is not expected to reproduce true from seed.

CHARACTERISTICS

The accompanying photos show a typical specimen of the plant according to this invention.

FIG. 1, exhibits the overall growth and flowering habit of *Raphiolepis indica* cv. Monto. Note the large glossy foliage, heavy flowering composed of broad panicles and the buff color of new foliage due to the tomentose covering.

FIG. 2, displays a closeup of the individual flowers composing a broad panicle. Note the pink petals at early anthesis which later fade to white along with the filaments which turn a contrasting red.

DESCRIPTION

Below is a detailed description of the new *Raphiolepis indica* cv Monto, the color terminology is from The British Horticultural Colour Charts.

Overall size and habit: Evergreen, dense, at four years of age, plant is approximately 4 feet in height and 4 feet in width.

Foliage:

*Size.*—Length varies from 5 to 7 cm; width to 3.5. to 4 cm.

*Shape.*—Varying from spatulate-obovate to elliptic with emarginate tip and attenuate base.

*Color.*—Upper-leaf-Spinach Green 0960/3. Underneath leaf-Scheeles Green 860/3.

*Margins.*—Entire on lower two-thirds of margin. Upper two thirds — serrate.

*Texture.*—Coriaceous.

*Arrangements.*—Alternate leaves at branch tips appear whorled.

*Pubescence.*—Lightly pubescent on new leaves, mature leaves shiny, glabrous.

*Petiole.*—1 to 2 cm in length.

Inflorescence:

*Size.*—Approximately 7 cm wide. Approximately 6 cm long.

*Shape.*—Broad pyramidal panicle.

*Broad.*—Bud 2 mm longer than calyx lobes color is a Phlox Pink 625/2, fully developed flower bud is Phlox Pink 625/3.

*Flower color.*—Petals are a Phlox Pink 635/3, suffused on all margins and at the base with Pastel Mauve 433/4. Before senescence flowers fade completely to Pastel Mauve 433/3 and filaments turn red.

*Petal size.*—Length: 10–11 mm (±1 mm). Width: 8 mm (±1 mm).

*Petal shape.*—Oblong — Spatulate. Tip obtuse; Base attenuate.

*Petal margin.*—Entire.

*Petal number.*—5 — single flower.

*Peduncle.*—Ranging in length 1.1–2.0 mm.

*Pedicel.*—7 to 8 mm pubescent.

*Calyx.*—5 lobes 4 to 5 mm in length, reflexed at flowering, wooly pubescent red tinge on calyx, lobes and bracts.

*Fragrance.*—Flower light sweet.

I claim:

1. A new and distinct selection of Raphiolepis as substantially shown and described herein, that is characterized by large glossy bright green leaves; brown tomentum covering the new foliage and large single pink flowers fading to pure white with red filaments.

* * * * *

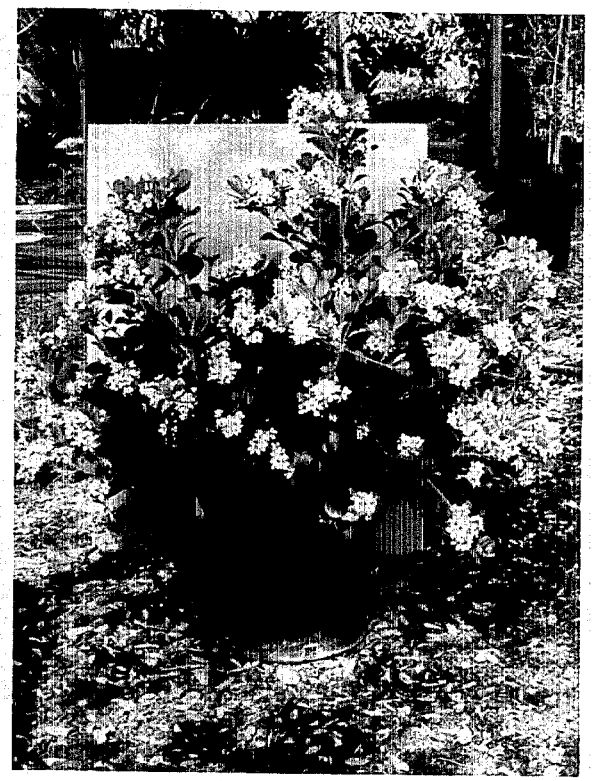
FIG. 1
FIG. 2
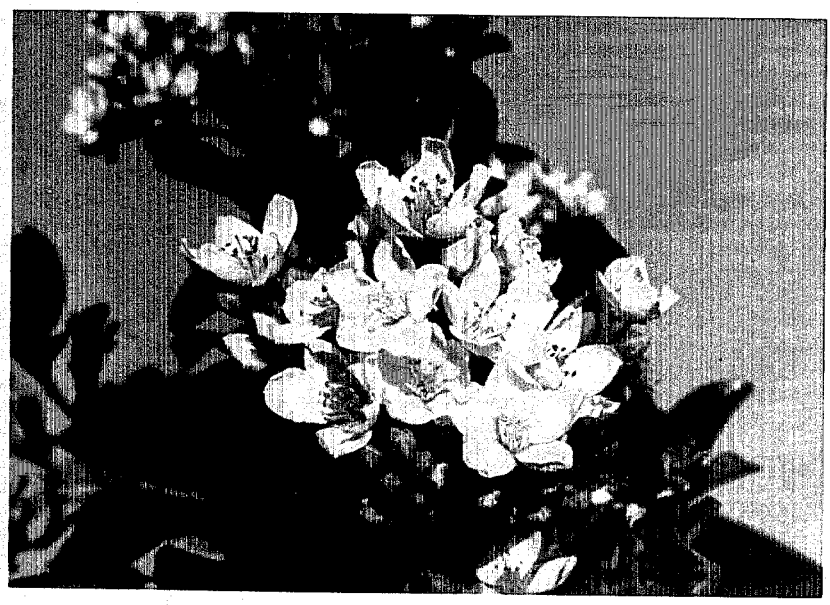

UNITED STATES PATENT AND TRADEMARK OFFICE

CERTIFICATE OF CORRECTION

PATENT NO. : Plant Pat. 05,862

DATED : January 20, 1987

INVENTOR(S) : Bill Ponto

It is certified that error appears in the above-identified patent and that said Letters Patent is hereby corrected as shown below:

Column 1, line 7, "Enchantress" should read -- Moness --.

Signed and Sealed this

Tenth Day of January, 1989

*Attest:*

DONALD J. QUIGG

*Attesting Officer*

*Commissioner of Patents and Trademarks*